United States Patent
Karlsson et al.

(10) Patent No.: US 9,770,346 B2
(45) Date of Patent: Sep. 26, 2017

(54) PROSTHETIC KNEE

(71) Applicant: OSSUR HF, Reykjavik (IS)

(72) Inventors: Sigurdur Gisli Karlsson, Kopavogur (IS); Sigurdur Olafsson, Reykjavik (IS); Sigurdur Hannesson, Kopavogur (IS)

(73) Assignee: OSSUR HF, Reykjavik (IS)

( * ) Notice: Subject to any disclaimer, the term of this patent is extended or adjusted under 35 U.S.C. 154(b) by 56 days.

(21) Appl. No.: 14/623,668

(22) Filed: Feb. 17, 2015

(65) Prior Publication Data

US 2015/0230942 A1 Aug. 20, 2015

Related U.S. Application Data

(60) Provisional application No. 61/940,986, filed on Feb. 18, 2014.

(51) Int. Cl.
| | | |
|---|---|---|
| *A61F 2/50* | (2006.01) | |
| *A61F 2/64* | (2006.01) | |
| *A61F 2/68* | (2006.01) | |

(52) U.S. Cl.
CPC .......... *A61F 2/64* (2013.01); *A61F 2002/503* (2013.01); *A61F 2002/5038* (2013.01);
(Continued)

(58) Field of Classification Search
CPC .. A61F 2/64; A61F 2/642; A61F 2/644; A61F 2/626; A61F 2002/5007;
(Continued)

(56) References Cited

U.S. PATENT DOCUMENTS

| | | | |
|---|---|---|---|
| 2,336,881 A | 12/1943 | Mortensen | |
| 3,723,997 A | 4/1973 | Kolman | |

(Continued)

FOREIGN PATENT DOCUMENTS

| | | |
|---|---|---|
| DE | 20 2005 021 906 U1 | 6/2011 |
| EP | 1 166 726 A1 | 1/2002 |

(Continued)

OTHER PUBLICATIONS

Medi USA. Medis OFM2-HD Knee Available with 275lb. Weight Limit. Oandp.com Dec. 2008.*
(Continued)

*Primary Examiner* — Thomas J Sweet
*Assistant Examiner* — Christie Bahena
(74) *Attorney, Agent, or Firm* — Workman Nydegger

(57) ABSTRACT

A prosthetic knee includes a housing, a chassis, and a brake member pivotally connected to the housing at a first location point and to the chassis at a second location point. A knee shaft extends through the brake member and is secured within a cavity defined by the housing. An extension assist system includes a biasing mechanism located inside of the chassis and an extension assist link. The extension assist link includes a body portion operatively connected to the biasing mechanism and a pair of arm portions situated in at least one slot defined by the knee shaft. The arm portions are pivotally connected to the knee shaft at a third location point located a distance from the first location point.

19 Claims, 8 Drawing Sheets

(52) U.S. Cl.
CPC ........... *A61F 2002/5039* (2013.01); *A61F 2002/5072* (2013.01); *A61F 2002/6854* (2013.01)

(58) Field of Classification Search
CPC ........ A61F 2002/503; A61F 2002/5073; A61F 2002/745; A61F 2002/5038; A61F 2002/5039; A61F 2002/5072; A61F 2002/6854
See application file for complete search history.

(56) References Cited

U.S. PATENT DOCUMENTS

| | | | |
|---|---|---|---|
| 3,982,279 A | | 9/1976 | Valenti et al. |
| 4,152,787 A | | 5/1979 | Meggyesy |
| RE31,673 E | | 9/1984 | Blatchford et al. |
| 4,578,083 A | | 3/1986 | Williams |
| 5,746,774 A | | 5/1998 | Kramer et al. |
| 5,899,943 A | * | 5/1999 | Shiraishi ............ A61F 2/64 623/39 |
| 6,159,248 A | | 12/2000 | Gramnas |
| 6,206,933 B1 | * | 3/2001 | Shorter ............ A61F 2/64 623/44 |
| 6,471,664 B1 | | 10/2002 | Campbell et al. |
| 7,544,214 B2 | | 6/2009 | Gramnas |
| RE42,903 E | | 11/2011 | Deffenbaugh et al. |
| 8,268,012 B1 | | 9/2012 | Cheng et al. |
| 2003/0050712 A1 | | 3/2003 | Shen |
| 2006/0259153 A1 | * | 11/2006 | Harn ............ A61F 2/644 623/44 |
| 2008/0281427 A1 | | 11/2008 | Shen |
| 2010/0100197 A1 | * | 4/2010 | Kremser ............ A61F 2/644 623/38 |
| 2011/0270415 A1 | | 11/2011 | Chen et al. |
| 2012/0150318 A1 | * | 6/2012 | Chabloz ............ A61F 2/64 623/33 |
| 2012/0310372 A1 | * | 12/2012 | Omarsson ............ A61F 2/644 623/43 |

FOREIGN PATENT DOCUMENTS

| | | |
|---|---|---|
| EP | 1 570 817 A1 | 9/2005 |
| WO | 2009/066055 A2 | 5/2009 |

OTHER PUBLICATIONS

Medi OFM2 (and Medi OFM2 view 2). Youtube. Published Oct. 11, 2012.*
International Search Report from Corresponding International PCT Application No. PCT/US2015/016075, May 19, 2015.

* cited by examiner

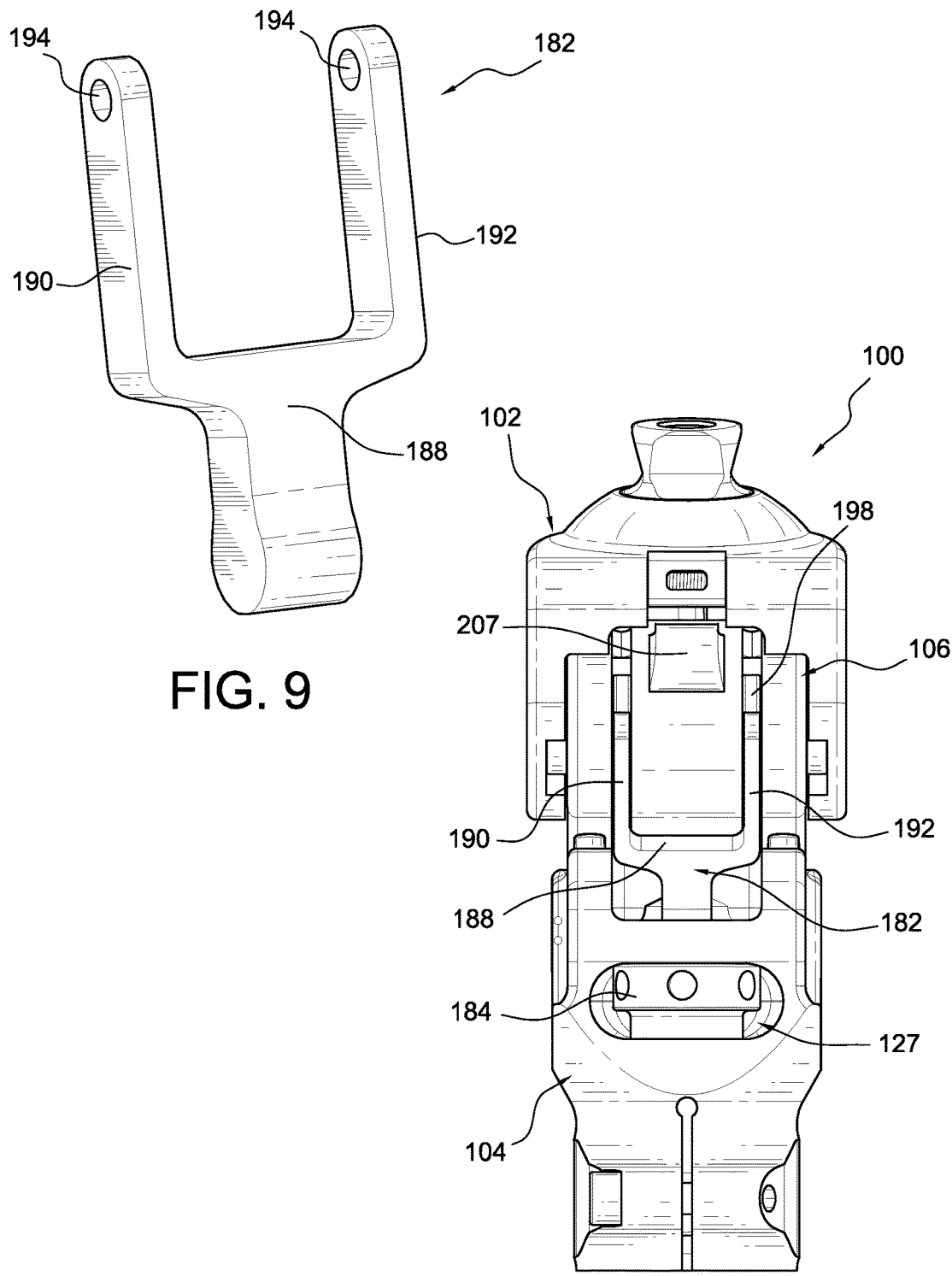

PROSTHETIC KNEE

TECHNICAL FIELD

The disclosure relates to a prosthetic knee for use with a prosthetic system.

BACKGROUND

Artificial limbs, including leg prostheses, employ a wide range of technologies to provide solutions suitable to many differing needs. For a trans-femoral amputee, basic needs in a leg prosthesis include stability, both while standing and during the stance phase of a walking gait, and mechanical compatibility with the walking (or running) gait, and some manner of knee flexion during stance and swing phases of a gait. Certain tradeoffs exist between security and stability and walking or running performance (dynamic behavior).

A simple, non-articulable leg prosthesis (having no movable knee) may provide maximum stability but does not provide for an ideal gait. Also, sitting may be awkward if a person cannot bend his knee. Available articulating prosthetic knees provide improved walking or running performance but are lacking in stability and control. They are also mechanically complex, expensive, or both. This can be especially problematic for low activity users, such as elderly or fresh amputees not yet very skilled in controlling the knee.

The amount of control or stability required can vary from user to user, while known prosthetic knees have no adjustability.

There is a need for a prosthetic knee that provides stability in stance and simulates more natural knee movement in swing.

SUMMARY

The disclosure describes various embodiments of a prosthetic knee providing a construction and design that facilitates stability in stance while also simulating more natural knee movement. The embodiments also can conveniently lock the knee in stance on demand.

The embodiments described can include a prosthetic knee that includes a housing, a chassis, and a brake member pivotally connected to the housing at a first location point and to the chassis at a second location point. The brake member prevents rotation of the housing relative to the chassis when the knee is loaded by a user instance, providing stability to the user. A knee shaft extends through the brake member and is secured within a cavity defined by the housing.

An extension assist system includes a biasing mechanism arranged to compress and push the knee back toward extension when the knee is in flexion, resulting in knee movement that is more natural and fluid. The biasing mechanism is located inside of the chassis and operatively connected to the knee shaft via an extension assist link.

The extension assist link includes a body portion operatively connected to the biasing mechanism and a pair of arm portions in at least one slot defined by the knee shaft. The arm portions are pivotally connected to the knee shaft at a third location point located a distance from the first location point. By connecting the arm portions to the knee shaft within the at least one slot, the extension assist link can advantageously distribute pressure and provide extra strength to the knee in supporting loads. The arm portions also provide additional support in the knee to resist bending moments.

According to a variation, the lower surface of the extension assist link defines a convex portion that is complementary shaped to a concave recess defined by the upper surface of a piston between the biasing mechanism and the extension assist link, providing consistent and smooth contact between the piston and the extension assist link.

According to a variation, a lock piece is pivotally connected to the housing and movable between a locked position in which the lock piece is engaged with a stop surface protruding from the brake member, and an unlocked position in which the lock piece is disengaged from the stop surface. In the locked position, the engagement between the lock piece and stop surface prevents rotation between the housing and the brake member substantially preventing flexion of the knee. The large contact surface area between the lock piece and stop surface reduces the lock piece inadvertently slipping off of the stop surface. This allows the knee to be safely and securely locked such as during training, rehabilitation, and or other particularly demanding situations. The lock piece can also be easily moved to the unlocked position, providing excellent control to the user.

According to a variation, a brake-play adjustment fastener is on the chassis that engages the brake member. Friction components of the knee may wear over time and develop brake play. If this occurs, the play at a contact point between the brake member and chassis should be adjusted. This can be adjusted using the brake-play adjustment fastener, which rotates the entire brake member around the first location point.

According to a variation, a brake sensitivity screw and biasing mechanism are within a screw hole formed in the brake member. The load required to activate the brake member can be advantageously regulated to the individual user's weight and preferences by changing the brake member preload using the brake sensitivity adjustment screw.

Additional features and advantages of embodiments of the present disclosure will be set forth in the description that follows, and in part will be obvious from the description, or may be learned by the practice of such exemplary embodiments.

BRIEF DESCRIPTION OF THE DRAWINGS

These and other features, aspects, and advantages of the present disclosure will become better understood regarding the following description, appended claims, and accompanying drawings.

FIG. 9 is an isometric view of the extension assist link removed from the prosthetic knee of FIG. 2 for ease of reference.

FIG. 10 is a back view of the prosthetic knee of FIG. 2.

DETAILED DESCRIPTION OF VARIOUS EMBODIMENTS

Figure 1:
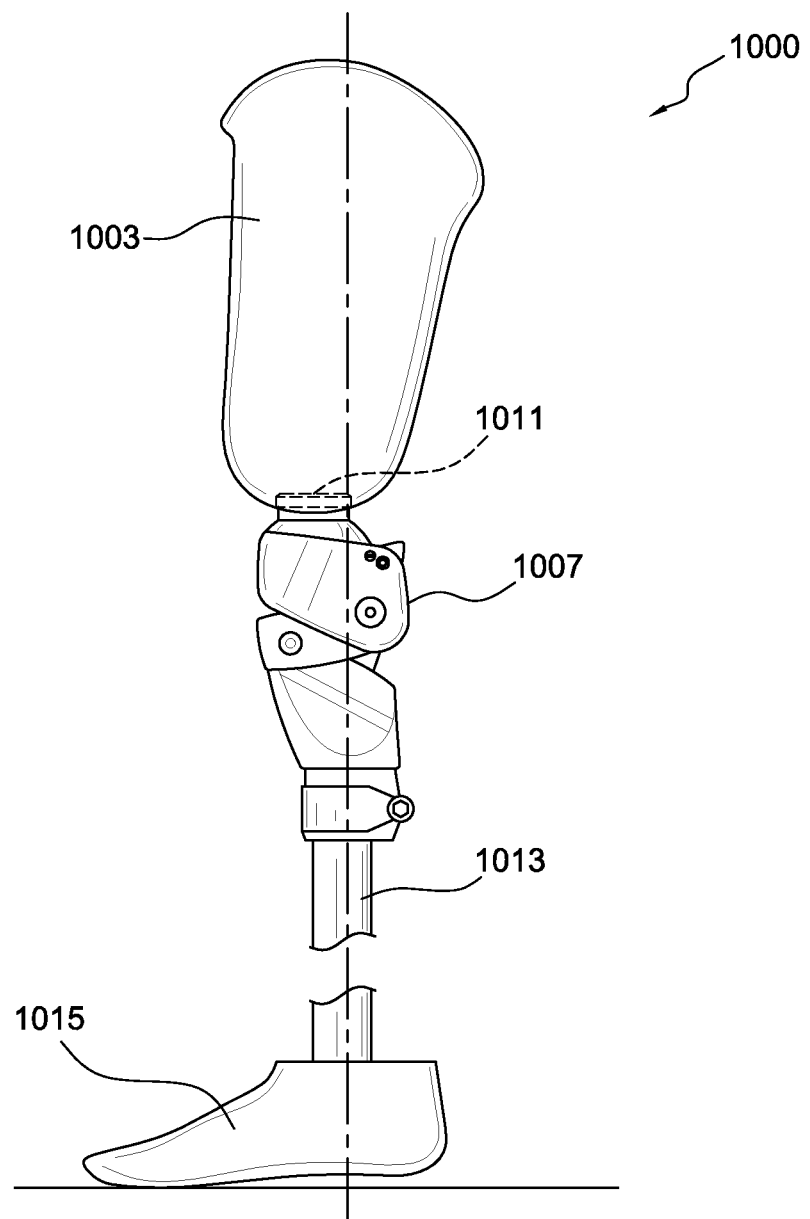
FIG. 1 is schematic view showing a prosthetic system.

A better understanding of different embodiments of the invention may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the embodiments disclosed, but on the contrary, the intention covers all modifications, alternative constructions, combinations, and equivalents falling within the spirit and scope of the disclosure.

For further ease of understanding the joint disclosed, a description of a few terms is necessary. The term "upper" has its ordinary meaning and refers to a location above, or higher than another location. Likewise, the term "lower" has its ordinary meaning and refers to a location below, or underneath another location. The term "posterior" also has its ordinary meaning and refers to a location behind or to the rear of another location. The term "anterior" has its ordinary meaning and refers to a location ahead or to the front of another location. Lastly, the terms "left" and "right" have their ordinary meaning and as used refer to the left and right sides when viewing the prosthetic knee from the anterior side.

FIG. 1 schematically depicts a prosthetic system 1000 for a residual limb. The system 1000 includes a socket assembly 1003 that embraces a residual limb, a prosthetic knee 1007 connected to the socket assembly 1003 by an adaptor 1011, a pylon 1013 connecting the knee 1007, and a foot 1015 connecting to the pylon 1013. The prosthetic knee 1007 can be any of the prosthetic knee disclosed embodiments.

In order to better understand the operation of the prosthetic knee described, a basic discussion of the gait cycle is provided. A gait cycle defines the movement of the leg between successive heel contacts of the same foot. The gait cycle has two phases: stance and swing. The stance phase has three time periods: heel-strike, mid-stance and toe-off. During mid-stance, the knee joint will be at full extension. An actual knee joint will have flexion between heel-strike and mid-stance and between mid-stance and toe-off. This is called "stance flexion." Not all prosthetic joints provide for stance flexion, and for those that do, they are mechanically complex, expensive, or both. These prosthetic joints typically require frequent maintenance and replacement. The amount of stance flexion required can vary from user to user, while most prosthetic knees have no adjustability.

Maximum flexion of the knee joint, while walking, will occur at the end of the toe-off phase. Maximum flexion is typically determined in part by the speed at which a person is walking. The faster a person walks the greater maximum flexion, while the slower a person walks, the lesser maximum flexion. In a natural knee, maximum flexion can be controlled and limited via the musculature of the leg. In a prosthetic knee joint, some artificial means of controlling and limiting maximum flexion are typically provided. Immediately following the end of the toe-off phase begins the swing phase.

While the stance phase has three time periods, the swing phase has two time periods: acceleration and deceleration. The acceleration phase begins immediately following the maximum flexion during the toe-off phase. During the acceleration phase, the lower portion of the leg, comprising the shin and foot, swings back towards full extension. In a natural knee joint, a deceleration phase follows the acceleration phase, during which the lower portion of the leg continues to swing towards full extension. Some prosthetic joints do not provide for any deceleration during the swing phase. Other prosthetic joints provide deceleration by using costly and bulky hydraulic or pneumatic cylinders. The deceleration required can vary from user to user, while most prosthetic joints have no adjustability.

Figure 2:
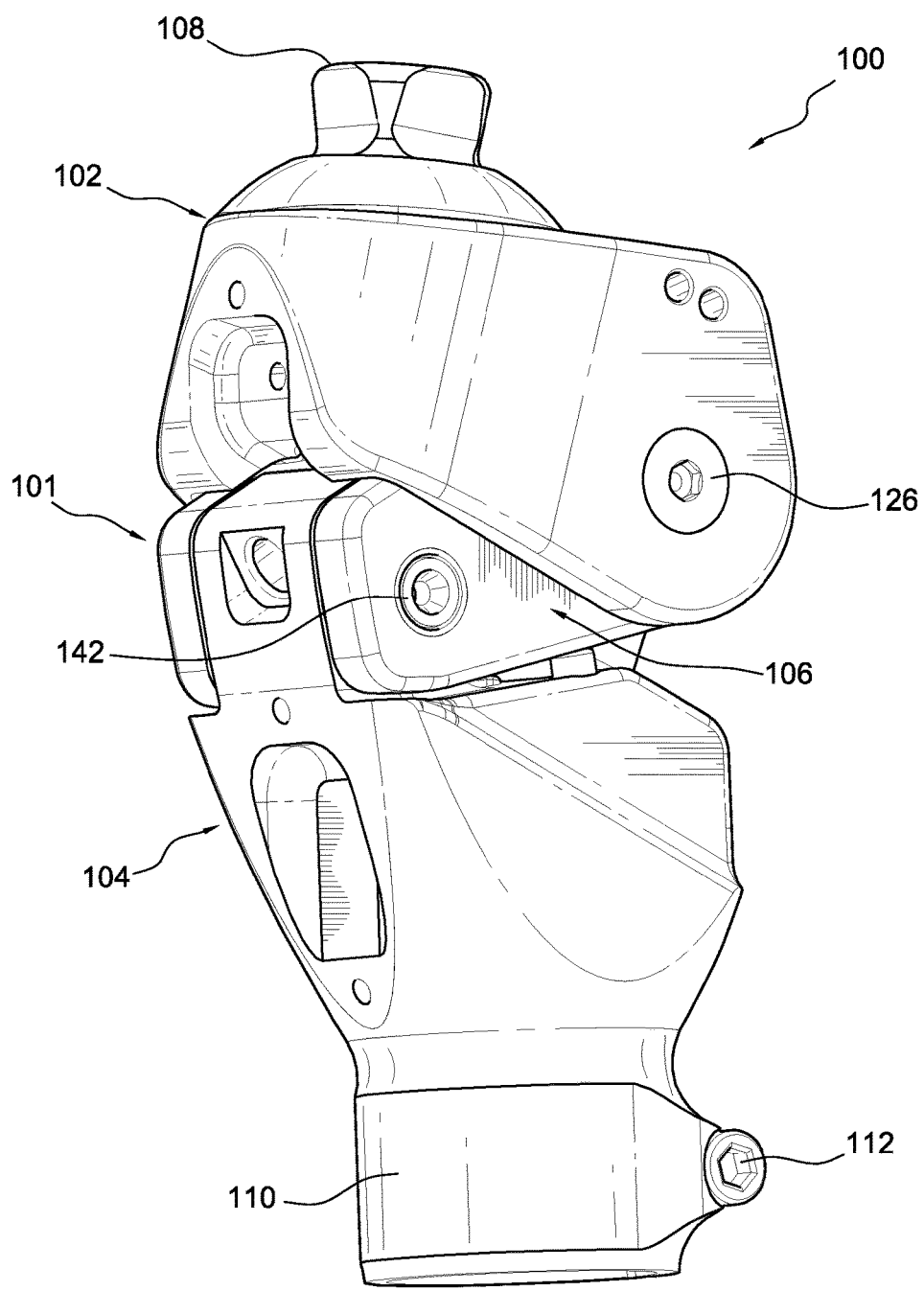
FIG. 2 is an isometric view of a prosthetic knee according to an embodiment.

FIGS. 2-13 illustrate a first embodiment of a prosthetic knee 100 for a prosthetic system or assembly. The knee 100 includes a housing 102, a chassis 104, and a load-dependent brake system 101 connecting the housing 102 and the chassis 104. As seen in FIG. 2, a pyramid adaptor 108 or a 4-prong adaptor can be positioned at a top of the housing 102 and a distal tube clamp attachment 110, having a socket head cap screw 112, for tightening can be positioned at the bottom of the chassis 104.

The load-dependent brake system 101 is arranged to selectively prevent rotation of the housing 102 relative to the chassis 104 when the knee 100 is loaded by a user in stance. When the load on the knee 100 is released, the load-dependent brake system 101 can be released so the knee 100 can swing or the housing 102 can rotate relative to the chassis 104. This advantageously provides more natural and controlled movement of the knee. The load-dependent brake system 101 can include a brake member 106, a knee shaft 122, and brake sleeve 160.

Figure 3:
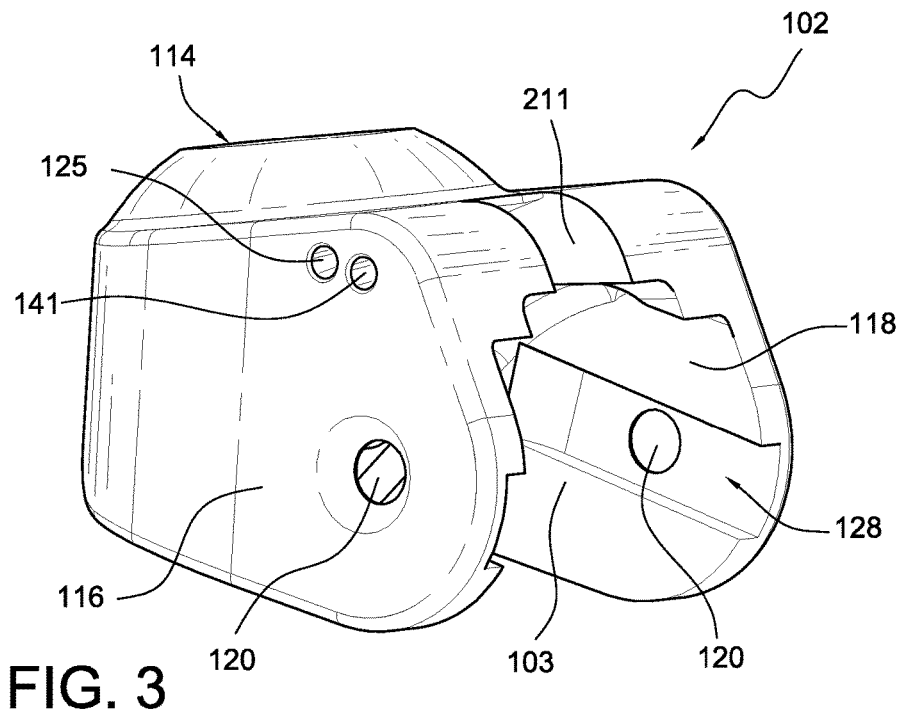
FIG. 3 is an isometric view of the housing removed from the prosthetic knee of FIG. 2 for ease of reference.

FIG. 3 shows the housing 102 removed from the knee 100 for ease of reference. The housing 102 includes a main body 114 with first and second flanges 116, 118 that protrude from the main body 114 towards the posterior or back of the housing 102. The housing 102 defines a cavity 103 in the bottom side thereof. The first flange 116 and the second flange 118 can be parallel to each other and can each include a fastener hole 120. The inner surface of each of the first and second flanges 116, 118 can define a keyway 128. The keyway 128 can be a generally rectangular slot or groove. The upper portion of the housing 102 defines a recess 211 and a pair of opposed retaining pin holes 125.

Figure 4:
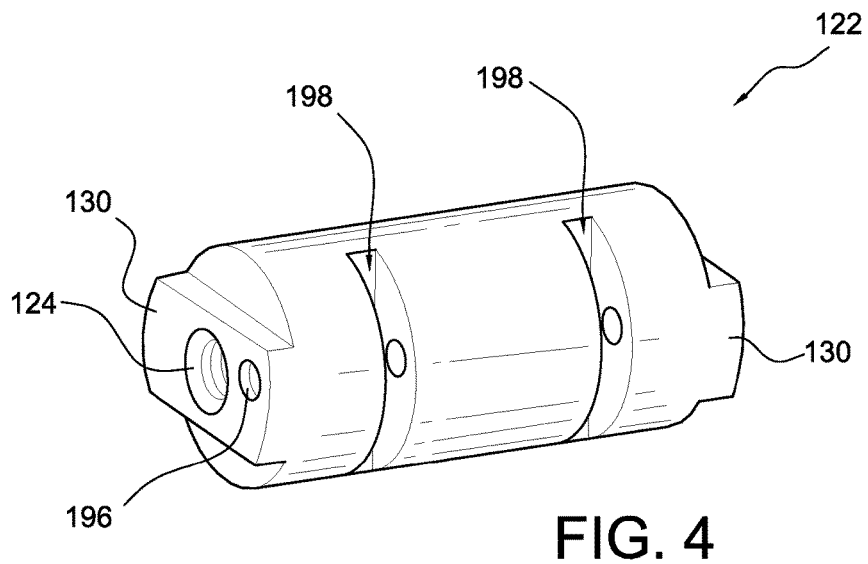
FIG. 4 is an isometric view of the shaft removed from the prosthetic knee of FIG. 2 for ease of reference.

Referring now to FIG. 4, the knee shaft 122 of the load-dependent brake system 101 is insertable within the cavity 103 of the housing 102 so the knee shaft 122 is located inside of the cavity 103, extending between the first and second flanges 116, 118. The knee shaft 122 is shown as a cylindrical body but can be any suitable shape. A fastener hole 124 can be defined in each end of the knee shaft 122.

The knee shaft 122 can be non-rotatably attached to the housing 102. For instance, the knee shaft 122 can be selectively retained within the cavity 103 of the housing 102 via at least one fastener 126 (shown in FIG. 2) respectively positioned in at least one fastener hole 120 of the housing and at least one of the fastener holes 124 defined in the knee shaft 122. A key 130 is defined on each end of the knee shaft 122.

When the knee shaft 122 is inserted into the cavity 103, the keys 130 slide into the keyway 128 defined by the housing. This prevents relative rotation between the knee shaft 122 and the housing 102. It also provides a solid connection between the knee shaft 122 and the housing 102 by increasing the contact surface area between them. It further aligns the fastener holes 120 and the fastener hole 124, facilitating assembly and/or disassembly of the knee 100.

The knee shaft 122 can define a through hole or pin hole 196 extending between its opposing ends. The pin hole 196 can be generally parallel and eccentrically positioned relative to a first location point 150 or knee axis (shown in FIG. 8) described below. A posterior surface of the knee shaft 122 can also define at least one slot 198 that intersects the pin hole 196 between the opposing ends of the knee shaft 122. The posterior surface of the knee shaft 122 is defined as being generally opposed an anterior surface of the knee shaft 122 facing the second location point 148.

As shown, the at least one slot can comprise a pair of slots 198. In other embodiments, the at least one slot 198 can comprise a single slot sized and configured to receive arm portions of the extension assist link described below. The pin hole 196 and the slots 198 are discussed in more detail below.

Figure 5:
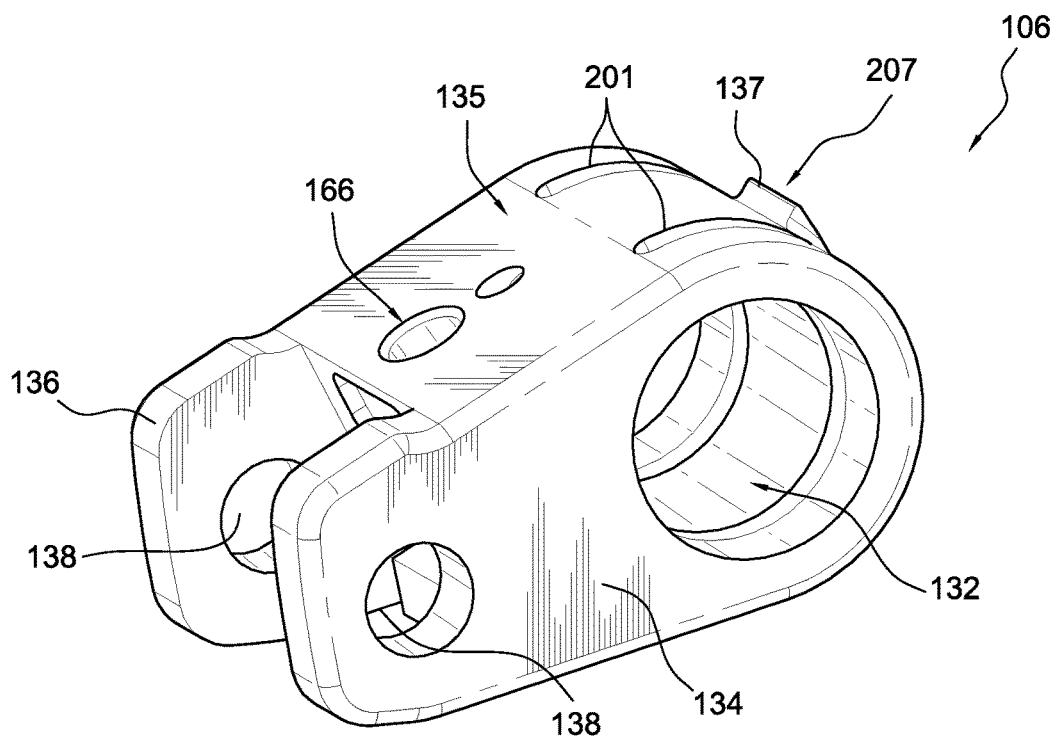
FIG. 5 is an isometric view of the brake clamp removed from the prosthetic knee of FIG. 2 for ease of reference.
Figure 6:
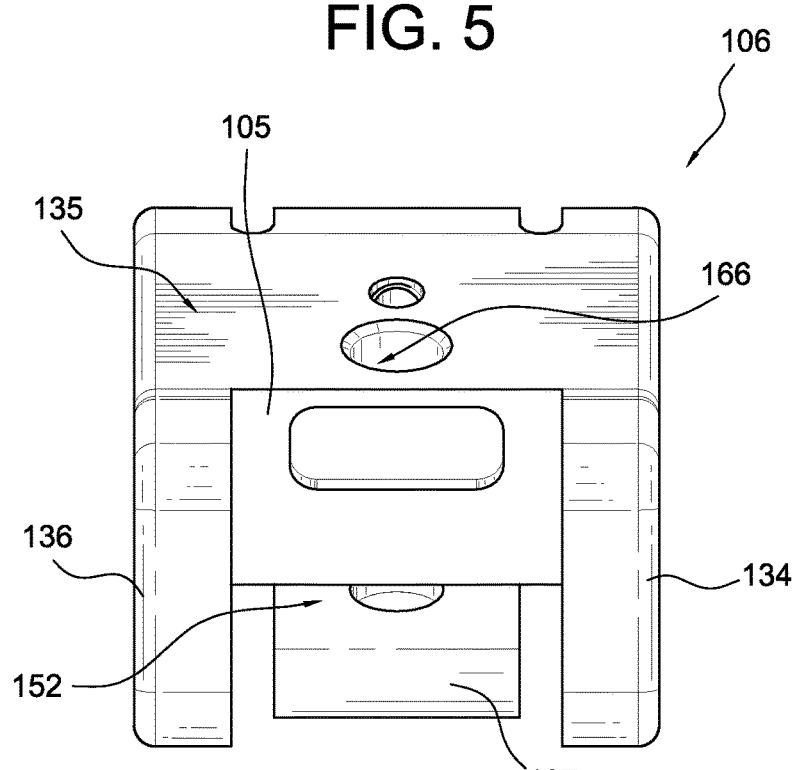
FIG. 6 is a front view of the brake clamp in FIG. 5.

Referring now to FIGS. 5 and 6, the brake member 106 can be a brake clamp movably connecting the housing 102 and the chassis 104 to one another. The brake clamp 106 can be pivotally connected to the housing 102 and pivotally connected to the chassis 104, allowing the housing 102 and the chassis 104 to be movably connected together.

The brake clamp 106 defines a main body 135 having an upper part 105 and a lower part 107 attached to the upper part 105. The upper part 105 can have a width that is greater than a width of the lower part 107. The brake clamp 106 defines side portions 134, 136 protruding from the upper part 105 towards the anterior of the brake clamp 106.

The side portions 134, 136 can be spaced apart and generally parallel to each other. A pivot pin hole 138 can be defined in each of the side portions 134, 136. A posterior surface of the brake clamp 106 defines a pair of slots 201 that generally correspond to the slots 198 of the knee shaft 122 when the knee shaft 122 is positioned within the cavity 103 of the housing 102. The posterior surface of the brake clamp 106 is defined as generally opposed an anterior surface of the brake clamp formed on the terminal ends of the side portions 134, 146.

A protruding step 207 can be defined on the brake clamp 106. The step 207 can be between the slots 201 defined in the brake clamp 106. The step 207 can have any suitable configuration but is shown as a substantially ramp-like protrusion forming a stop surface 137 and an upper curved surface. The stop surface 137 extends generally perpendicular to the outer radial surface of the brake clamp 106. This can create more normal contact between the step 207 and a lock piece described below, reducing the lock piece inadvertently sliding off the step 207. The upper curved surface of the step 207 helps the lock piece to slide or move past the step 207 until the knee 100 reaches full extension. In other embodiments, the step 207 can be a generally rectangular member, a triangular member, or any other appropriate member.

The step 207 can be attached to the brake clamp 106 or integrally formed on the brake clamp 106. The step 207 can have a width that is less than a width of the brake clamp 106. The width of the step 207 can generally correspond to a width of the recess 211 in the housing 102.

The brake clamp 106 also defines a shaft hole 132 extending therethrough. The shaft hole 132 can be generally parallel to the pivot pin holes 138. At least a portion of the brake clamp 106 is positionable within the cavity 103 of the housing 102, with the knee shaft 122 extending through the shaft hole 132. The brake clamp 106 can also define a slot 152 between the upper part 105, the lower part 107, and a contact pad 154 attached to a bottom side of the lower part 107.

The knee shaft 122 is rotatably received within the shaft hole 132 such that relative rotation between the housing 102 and the brake clamp 106 is possible. For instance, the housing 102 and the knee shaft 122 are rotatable about the first location point 150 extending through the knee shaft 122. Optionally, washers and/or bushings can be provided on the knee shaft 122 between the components of the knee 100 to help properly align, space, and/or fasten the individual components of the knee 100.

Figures 7, 8:
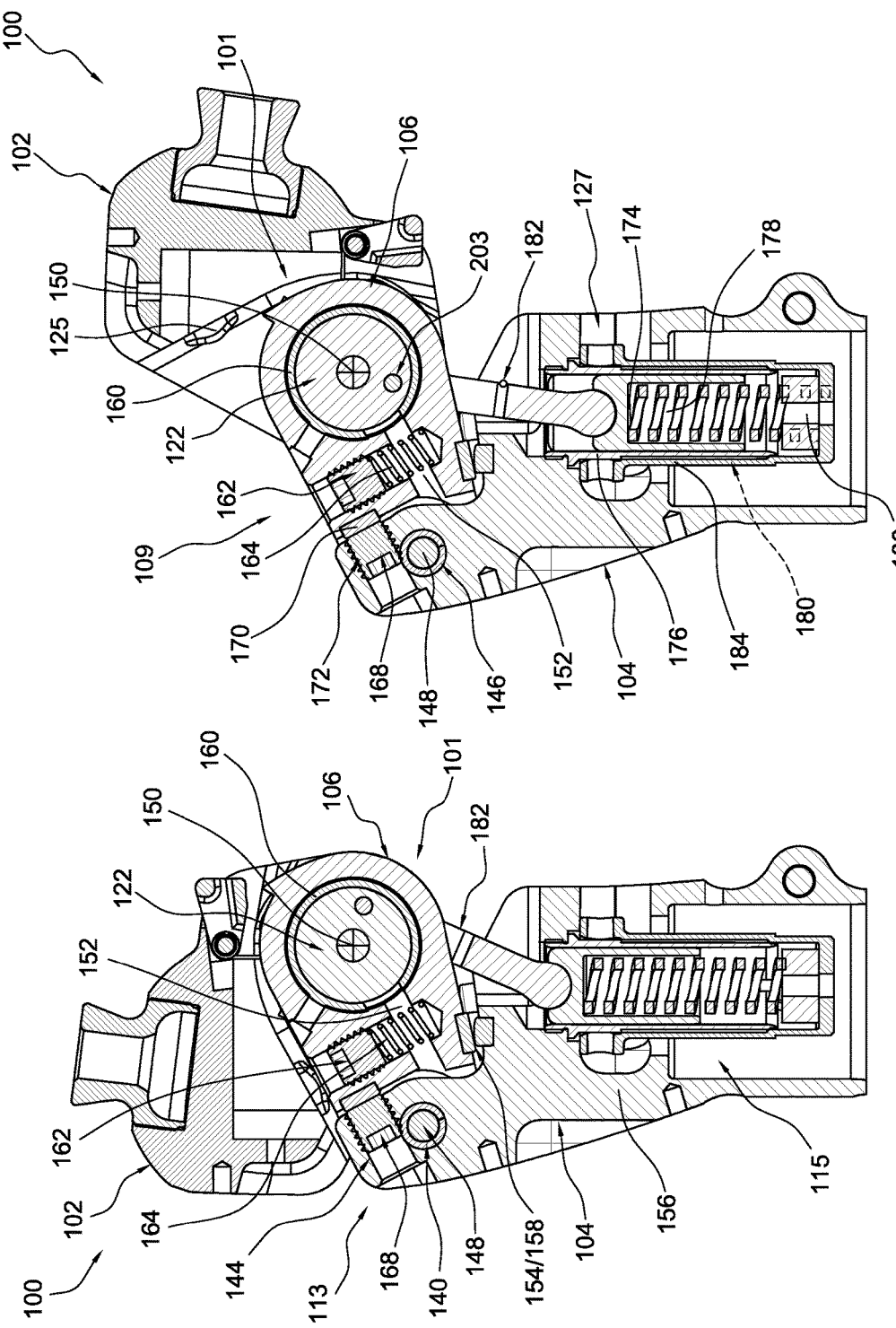
FIG. 7 is a cross-sectional view of the prosthetic knee of FIG. 2 in full extension according to an embodiment.
FIG. 8 is a cross-sectional view of the prosthetic knee of FIG. 2 in flexion according to an embodiment.

As seen in FIGS. 7 and 8, the chassis 104 defines a main body 156 and an upper portion 144 upwardly extending therefrom. The upper portion 144 defines a pivot pin hole 146 passing therethrough. A pivot pin 140 can be retained at each end by bearings 142 respectively positioned in the pivot pin holes 138 of the brake clamp 106. The pivot pin 140 passes through the pivot pin holes 138 and the pivot pin hole 146. The upper portion 144 of the chassis 104 is pivotally between the side portion 134 and the side portion 136 of the brake clamp 106. The chassis 104 includes a contact pad 158 attached to an upper side of the main body 156.

The basic brake function of the load-dependent brake system 101 will now be explained. When the knee 100 is loaded (e.g., foot on the ground) as shown in FIG. 7, the load-dependent brake system 101 moves to a braked configuration or state in which a second location point 148 or actuation axis allows relative rotation between the brake clamp 106 and the chassis 104, which loads a contact point between the contact pad 154 on the brake clamp 106 and the contact pad 158 on the chassis 104. This causes compression of the slot 152 defined by the brake clamp 106, which causes compression of the brake sleeve 160, which is fixedly attached to the brake clamp 106.

The brake sleeve 160 is disposed within the shaft hole 132 and between the brake clamp 106 and the knee shaft 122. Compression of the brake sleeve 160 on the knee shaft 122 creates friction against the knee shaft 122, preventing rotation of the knee 100 about the first location point 150. More particularly, compression of the brake sleeve 160 creates friction that prevents rotation of the housing 102 about the first location point 150. The brake sleeve 160 can be a C-shaped brake sleeve or any other appropriate brake sleeve. The brake sleeve 160 may be formed of metal such as copper, rubber, or any other material which would provide sufficient compression when the knee is loaded.

When the load is released from the knee 100, the load-dependent brake system 101 can move to a released configuration or state, in which the slot 152 and the brake sleeve 160 decompress, allowing the knee 100 to swing around the first location point 150 to the flexion position in FIG. 8.

A brake sensitivity adjustment system 109 can adjust the load required to activate the load-dependent brake system 101. The brake sensitivity adjustment system 109 includes a brake sensitivity adjustment screw 162 and a biasing mechanism 164. The biasing mechanism 164 can be a spring or any other suitable resilient member. The brake sensitivity adjustment screw 162 and the biasing mechanism 164 can be arranged within an adjustment screw hole 166 (FIG. 6) defined in the brake clamp 106. The biasing mechanism 164 can be within the adjustment screw hole 166 between the lower part 107 and the brake sensitivity adjustment screw 162. The biasing mechanism 164 engages the lower part 107 of the brake clamp 106 and extends across the slot 152 to where it engages the brake sensitivity adjustment screw. The biasing mechanism 164 adjusts the load required to compress the slot 152 when the brake sensitivity adjustment screw 162 is turned.

Turning the brake sensitivity adjustment screw 162 in a first direction (tightening), compresses the biasing mechanism 164, increasing the compression preload of the brake clamp 106 or the force required to close the slot 152 of the brake clamp 106. Turning the brake sensitivity adjustment screw 162 in a second direction (loosening), allows the biasing mechanism 164 to decompress, decreasing the compression preload of the brake clamp 106. By adjusting the compression preload of the brake clamp 106, the load required to activate the knee brake can be regulated to the individual user's weight and/or preferences, providing more natural and controlled movement of the knee 100.

A brake-play adjustment system 113 can adjust play that may develop in the load-dependent brake system 101. The brake-play adjustment system 113 can include a brake-play adjustment fastener or screw 168 and a contact pad 170. The brake-play adjustment screw 168 extends into a hole 172 defined in the upper portion 144 of the chassis 104. The contact pad 170 is secured within a recess defined on the anterior of the brake clamp 106. The brake-play adjustment screw 168 is arranged to adjustably engage the contact pad 170 on the brake clamp 106.

Different components of the load-dependent brake system 101 may wear over time and develop brake-play (e.g., an unwanted slight rotation in the braked state). If this occurs, the play can be adjusted by using the brake-play adjustment screw 168. For instance, turning the brake-play adjustment screw 168 in a first direction (tightening) advances the brake-play adjustment screw 168 within the hole 172, engaging the contact pad 170 on the brake clamp 106. This engagement creates a moment around the second location point 148, which rotates the brake clamp 106 relative to the chassis 104 about the second location point 148. The position of the brake clamp 106 relative to the chassis 104 can be controlled and/or regulated, helping to maintain the contact point between the contact pad 154 on the brake clamp 106 and the contact pad 158 on the chassis 104, which limits play in the load-dependent brake system 101.

In swing phase, the knee 100 is returned to full extension via an extension assist system 115. A central component of the extension assist system 115 is a biasing mechanism or extension assist spring 178 compressed when the knee 100 is flexed, and pushes the knee 100 back to extension. The extension assist spring 178 is located inside the chassis 104 and operatively connected to the knee shaft 122 via a piston 174 and an extension assist link 182.

The piston 174 and extension assist spring 178 are retained within an extension assist housing including an inner housing 176 secured within a cavity 180 defined in the main body 156 of the chassis 104. The extension assist housing can also include an external housing 184 provided coaxially with the inner housing 176 in the cavity 180. The external housing 184 is arranged to receive the inner housing 176, the piston 174, and a spring guide 186 and the extension assist spring 178.

In some embodiments, the external housing 184 can be adjustable. For instance, a clinician or user can rotate the external housing 184, moving it in an axial direction (e.g., upwards or downwards) to alter the compression of the extension assist spring 178. This can vary the biasing force applied to the piston 174 by the extension assist spring 178, and the biasing force applied to an extension assist link 182 by the piston 174. The level of biasing force generated by the extension assist system 115 on the knee 100 toward extension can be adjusted as desired or for example, to the user's walking speed.

Stored mechanical energy within the extension assist spring 178 when compressed can be adjusted by rotating the external housing 184 via an opening 127 defined in the posterior or rear of the chassis 104. This advantageously allows the extension assist system 115 to be adjustable and/or accessible to the user or clinician without having to disassemble the knee 100. For instance, a clinician can adjust the compression of the extension assist spring 178 without having to remove a pylon from the distal tube clamp attachment 110 of the chassis 104.

The extension assist link 182 can exhibit any suitable configuration but is shown in FIG. 9 having a body portion 188 and first and second arm portions 190, 192 protruding from the body portion 188. The body portion 188 can connect the first and second arm portions 190, 192 to one another. The body portion 188 can include a cross member extending between the arm portions 190, 192 and a base extending generally downward from the cross member to a distal end or lower surface of the extension assist link 182.

The first and second arm portions 190, 192 are shown generally parallel to each other, each defining a pin hole 194. A lower surface of body 188 of the extension assist link 182 can define a convex portion that is complementary shaped to a concave recess defined by the upper surface of the piston 174, providing consistent and smooth surface contact between the piston 174 and the extension assist link 182.

As best seen in FIG. 10, the arm portions 190, 192 of the extension assist link 182 can be within the slots 198 defined in the knee shaft 122. The slots 198 can advantageously accommodate movement of the arm portions 190, 192 relative the knee shaft 122 and help limit rotation of the knee shaft 122.

The extension assist link 182 can be pivotally connected to the knee shaft 122 at a third location point 203 (best seen in FIG. 8) within the slots 198. The arm portions 190, 192 can be symmetric regarding the central plane of rotation. By connecting the arm portions 190, 192 to the knee shaft 122 with the slots 198, the extension assist link 182 can advantageously distribute pressure and provide extra strength to the knee 100 in supporting loads. The extension assist link 182 is also advantageous since the arm portion 190 is connected to the arm portion 192 by the body portion 188, providing additional support in the knee 100 to resist a bending moment.

The third location point 203 is located a distance from the first location point 150, about which the knee shaft 122 and the housing 102 rotate. This creates an eccentric connection between the extension assist link 182 and the knee shaft 122. Rotation of the knee shaft 122 moves the extension assist link 182 in an upward direction or a downward direction. The third location point 203 can comprise a connection pin extending through the pin holes 194 in the extension assist link 182 and the pin hole 196 in the knee shaft 122. The slots 201 defined in the brake clamp 106 can accommodate movement of the arm portions 190, 192 relative to the brake clamp 106.

In the swing phase or when the knee 100 is brought from the extension position (shown in FIG. 7) to the flexion position (shown in FIG. 8), the load-dependent brake system 101 is in the release state and the housing 102 and knee shaft 122 can rotate about the first location point 150. Because the extension assist link 183 is eccentrically connected to the shaft, this rotation moves the extension assist link 183 and the piston 174 in a downward direction, compressing the extension assist spring 178 within the cavity 182.

The stored mechanical energy in the extension assist spring 178 then moves the extension assist spring 178 back toward its equilibrium position, which pushes the piston 174 in an upward direction. This forces the extension assist link 182 away from the spring guide 186, causing the knee shaft 122 and the housing 102 to rotate about the first location point 150, which forces the knee 100 back toward the extension position.

Figure 11:
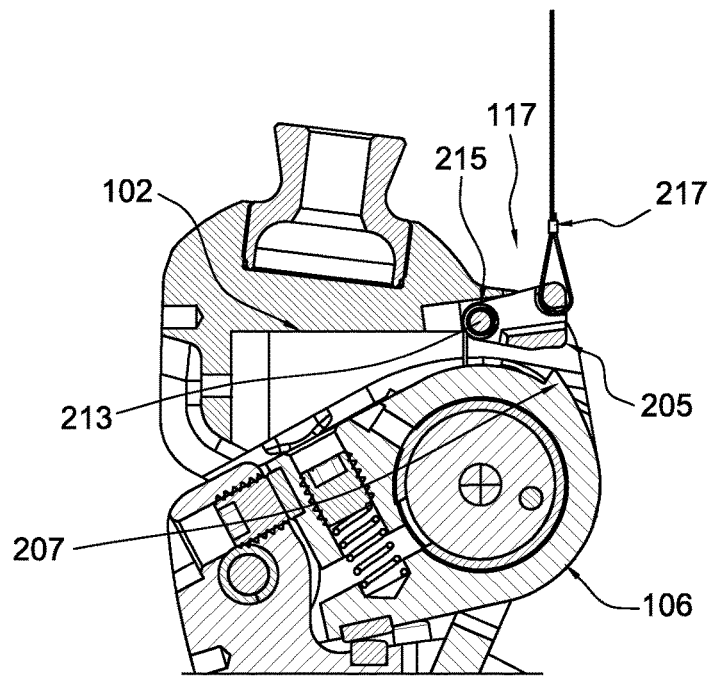
FIG. 11 is a detailed cross-sectional view of the prosthetic knee of FIG. 2 showing the manual lock mechanism.
Figure 12:
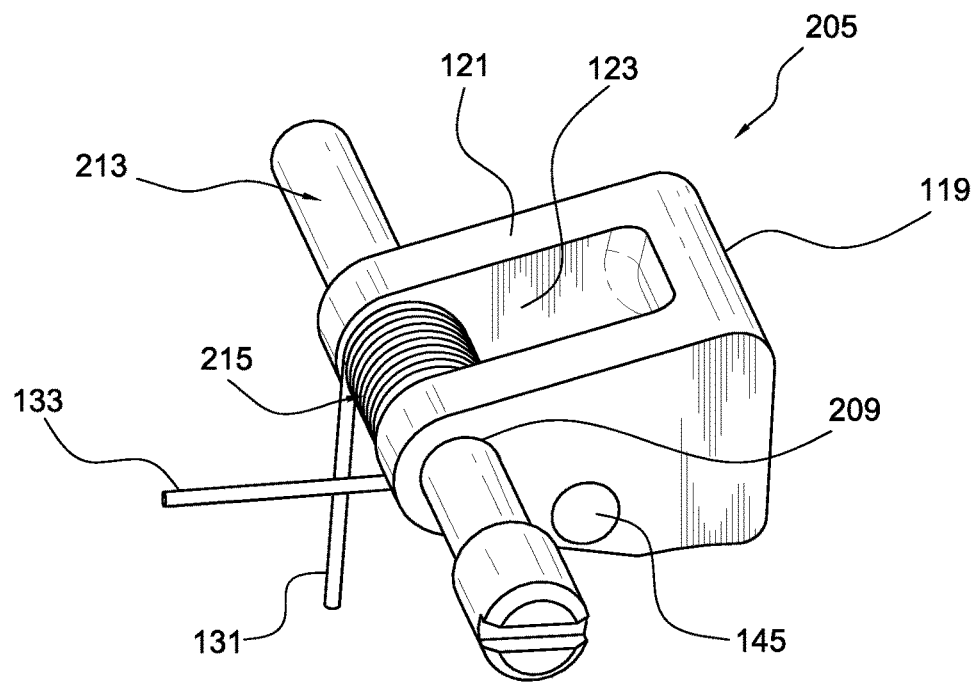
FIG. 12 is an isometric view of the manual lock mechanism removed from the prosthetic knee of FIG. 2 for ease of reference.

Referring to FIGS. 11 and 12, the knee 100 can include a locking system 117 allowing the knee 100 to be completely locked in one or more different positions. The manual locking system 117 can include a lock piece 205 and the step 207 defined on the brake clamp 106.

The lock piece 205 can have any shape but is shown having a generally wedge-like shape. The lock piece 205 has a body portion 119, first and second side arm portions 121 extending from the body portion 119, and a gap 123 defined between the side arm portions 121. Each of the side arm portions 121 can define a pin hole 209 extending therethrough.

The lock piece 205 can be within the recess 211 (FIG. 3) defined by the housing 102 and pivotally connected to the housing 102 via a retaining pin 213 extending through the pin holes 209. Opposing ends of the retaining pin 213 can be within the retaining pin holes 125 in the housing 102. The lock piece 205 can be fixedly attached to the retaining pin 213 so the lock piece 205 and the retaining pin 213 rotate together. Alternatively, the lock piece 205 can be rotatably attached to the retaining pin 213 so the lock piece 205 can rotate relative to the retaining pin 213. The retaining pin 213 can be integral to the lock piece 205 or the retaining pin 213 can be separate from the lock piece 205.

The lock piece 205 is rotatable between an unlocked position and a locked position. In the unlocked position, the lock piece 205 is rotated away from the brake clamp 106 so the lock piece 205 clears the step 207, allowing flexion or movement of the knee 100.

In the locked position, the lock piece 205 is rotated toward the brake clamp 106 and engages the stop surface 137 of the step 207. This prevents flexion of the knee 100, advantageously limiting movement of the knee 100 during training, rehabilitation, and/or other particularly demanding situations.

The posterior surface of the lock piece 205 may have a geometric shape which corresponds to the stop surface 137 defined by the step 207. For instance, the posterior surface of the lock piece 205 and the stop surface 137 can both be planar or can form complementary angles. In other embodiments, the stop surface 137 can include a slot or groove configured to receive a key member defined on the lock piece 205. In other embodiments, the stop surface 137 can include a concave portion corresponding to a convex portion of the posterior surface of the lock piece 205. The posterior surface of the lock piece 205 can be defined as being generally opposed the portion of the lock piece carrying the retaining pin 213.

The step 207 can be molded on the surface of the brake clamp 106, which can have a solid construction protruding from a profile of the brake clamp 106 or the outer portion of the brake clamp 106 at the base of the step 207. As seen, the lock piece 205 can also have a construction arranged to resist deformation or failure, helping to provide solid contact between the lock piece 205 and the stop surface 137. The size of the stop surface 137 and/or step 207 extending above the profile of the brake clamp 106 also forms a larger contact surface area between the stop surface 137 and the lock piece 205, reducing the lock piece 205 inadvertently slipping off of the step 207.

At least one the lock piece 205 or the step 207 can have a wider or thicker configuration, providing a greater locking strength. The stop surface 137 and/or the lock piece 205 can be formed from metal, plastic, or another rigid material providing solid contact.

The lock piece 205 can be biased toward the locked position. For instance, a biasing mechanism or torsion spring 215 can be loaded on the retaining pin 213 and positioned between the side arm portions 121 of the lock piece 205. The torsion spring 215 can include a first arm 131 insertable in a small hole formed in the brake clamp 106 and a second arm 133 arranged to engage the housing 102. Stored mechanical energy in the torsion spring 215 biases the lock piece 205 toward the locked position.

Figure 13:
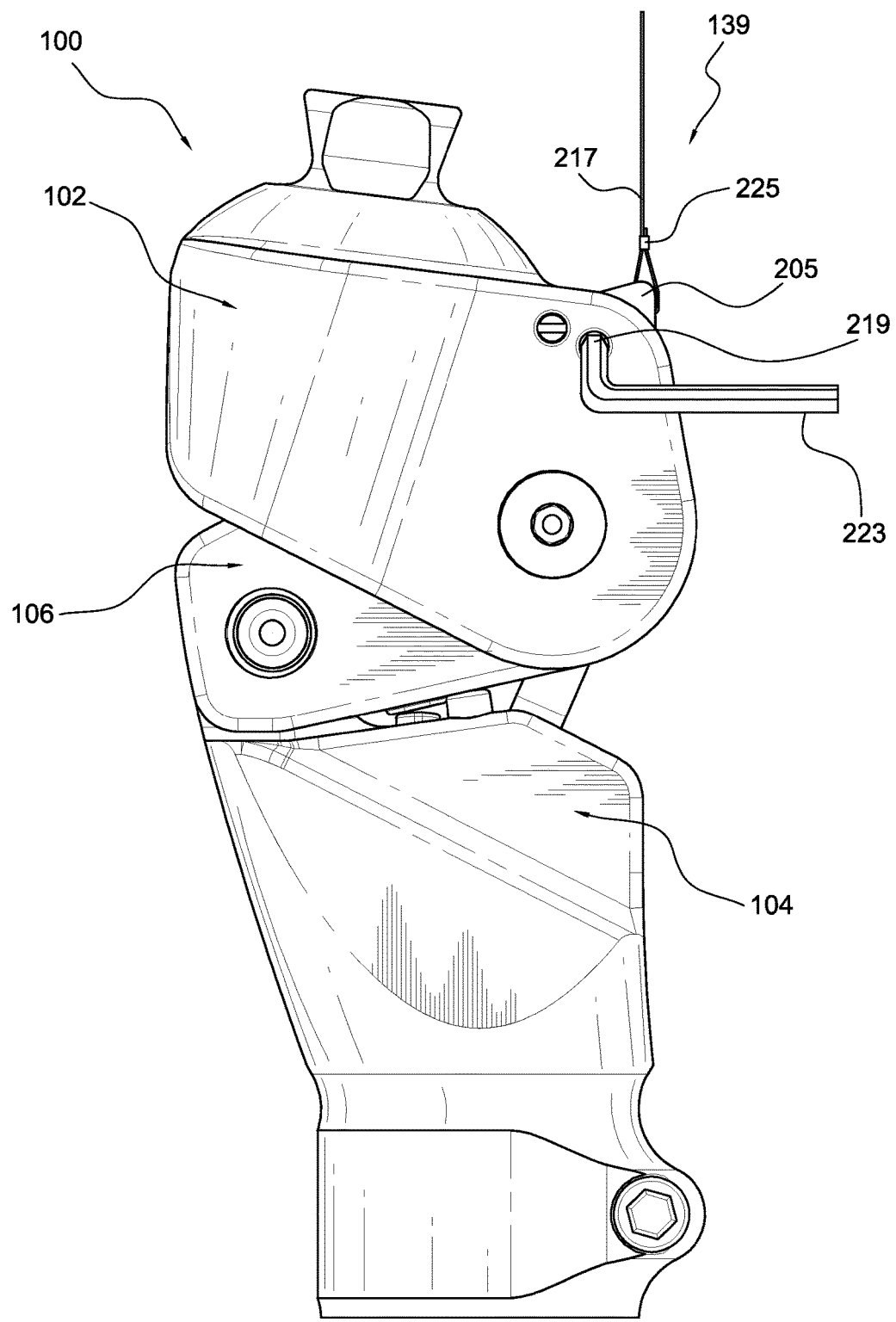
FIG. 13 is a side view of the prosthetic knee of FIG. 2.

A release system 139 can allow a user or clinician to manually move the locking system 117 to the unlocked position. For instance, when the lock piece 205 is in the locked position, and hence the knee 100 in a locked state, sitting down can be difficult. The release system 139 can allow a user to release the lock piece 205 from the locked position to the unlocked position. As seen in FIG. 13, the release system 139 can include a lanyard, tether, or cable 217 attached to the lock piece 205 that includes a handle portion. The cable can be threaded through the lock piece 205. A user can thread a distal end of the cable 217 through a fastener 225 having a tubular configuration, through the lock piece 205, and back through the fastener 225. The user can then adjust the length of the cable 217 as desired. With the length of the cable 217 adjusted, the user then can secure (e.g., crimp) the fastener 225 on the cable 217, securely attaching the cable to the lock piece 205.

To manipulate the release system 139, the user can pull on the cable handle to lift the lock piece 205 to the unlocked position. When the user releases the cable, the lock piece 205 can return to the locked position when the knee 100 reaches full extension, allowing the lock piece 205 to engage the stop surface 137 defined on the step 207. Optionally, the retaining pin 213 includes a head portion defining a recess arranged to receive a tool. The tool can manually rotate the retaining pin 213 which if fixedly attached to the lock piece 205 will rotate the lock piece 205.

The locking system 117 can include a locking feature arranged to selectively deactivate the lock piece 205. As seen in FIGS. 12 and 13, a set screw 219 can be disposed within a hole 141 (best seen in FIG. 3) defined in the housing 102. The set screw 219 is arranged to selectively engage a recess 145 defined in the lock piece 205.

To deactivate the locking function of the lock piece 205, a user can pull on the cable 217 or lift the lock piece 205 while tightening the set screw 219 such that it engages the recess 145 on the lock piece 205, preventing movement of the lock piece 205 into the locked position.

To activate the locking function of the lock piece 205, the user can unscrew the set screw 219 until it disengages from the recess 145. Optionally, the set screw 219 can be turned using a hex key 223 in FIG. 14 or another appropriate type of tool.

Alternatively, the housing 102 can define a plurality of holes so rotation of the locking piece 205 can be locked in a number of different positions.

In other embodiments, the lock piece can have a generally triangular shape, a generally rectangular shape, or any other suitable shape. In other embodiments, the extension assist link can have any suitable configuration such as a bar, a rod, an H-like member, or any other appropriate linking structure. Further, while the extension assist mechanism is described including an extension assist spring, in other embodiments, the extension assist mechanism can include a resiliently compressible member/material, an elastic member, or any other appropriate member. In addition, while the load-dependent brake system is described including a brake clamp, in other embodiments, the brake clamp 106 can be omitted. The knee can load-dependent brake system comprising a load-dependent ratchet mechanism connecting the housing and the chassis, a friction based brake mechanism, a torsion spring type brake mechanism, a locking cam-type brake mechanism, combinations thereof, or any other suitable load-dependent brake system. The knee can include a single axis knee or the knee can include multiple knee axes.

While the load-dependent brake system is described including a brake clamp, other types of braking mechanisms are possible. For instance, the brake clamp can be omitted and the knee can include a load-dependent ratchet mechanism connecting the housing and the chassis. In other embodiments, the knee can include a friction based brake mechanism, a torsion spring type brake mechanism, combinations thereof, or other suitable type of load-dependent brake system.

Further, the brake sensitivity adjustment system is described comprising a brake adjustment screw and resilient member, however, it will be appreciated that other types of brake sensitivity adjustment systems are possible. For instance, the brake sensitivity adjustment system can include one or more interchangeable resilient members or springs disposed within the sensitivity adjustment screw hole between the lower part of the brake clamp and a plug member. The one or more springs can be selected based on one or more properties (e.g., stiffness) to achieve a desired compression preload of the brake clamp. While the brake-play adjustment system is described including a play adjustment screw and play adjustment contact pad, in other embodiments, the brake-play adjustment system can include any suitable play adjustment mechanism.

In other embodiments, the lock mechanism can be formed at different locations on the knee so the knee can be locked in positions other than full extension. In other embodiments, the lock mechanism can include a torsion bar or any other suitable resilient member to bias the lock piece.

While the foregoing embodiments have been described and shown, alternatives and modifications of these embodiments, such as those suggested by others may be made to fall within the scope of the invention. While the hinge has been described in combination with a knee brace, it will be understood that the principles described may be extended to other types of orthopedic and prosthetic devices.

The invention claimed is:

1. A prosthetic knee comprising:
a housing;
a chassis;
a brake member pivotally connected to the housing at a first location point and to the chassis at a second location point, the brake member defining a first pair of slots along a posterior surface of the brake member and a protruding step between the first slots;
a knee shaft extending through the brake member and secured within a cavity defined by the housing, the knee shaft defining a second pair of slots along a posterior surface of the knee shaft corresponding in location to the first slots;
an extension assist system including:
a biasing mechanism located inside the chassis; and
an extension assist link including a body portion operatively connected to the biasing mechanism and a pair of arm portions situated in the first slots defined in the brake member and in the second slots defined in the knee shaft, the arm portions pivotally connected to the knee shaft at a third location point located within the second slots and a distance from the first location point.

2. The prosthetic device of claim 1, further comprising a piston secured between and engaging the biasing mechanism and the extension assist link.

3. The prosthetic device of claim 2, wherein a lower surface of the extension assist link defines a convex portion that is complementary shaped to a concave recess defined by the upper surface of the piston for engagement therewith.

4. The prosthetic knee of claim 2, further comprising:
an extension assist housing situated in the chassis and receiving the piston and the biasing mechanism, wherein the position of the extension assist housing within the chassis is adjustable to adjust a biasing force exerted on the knee by the biasing mechanism.

5. The prosthetic knee of claim 1, further comprising:
a pylon attached to the chassis; and
an opening defined in a rear of the chassis, the opening arranged to provide access for adjusting compression of the biasing mechanism without removal of a pylon from the prosthetic knee.

6. The prosthetic knee of claim 1, further comprising a brake sleeve interposed between the brake member and the knee shaft.

7. The prosthetic knee of claim 6, wherein when the knee is loaded by the user a contact point is loaded between the housing and the chassis to compress the brake member and the brake sleeve about the knee shaft to create friction between the brake sleeve and the knee shaft to substantially prevent rotation of the housing about the first location point.

8. The prosthetic knee of claim 1, further comprising a lock piece pivotally connected to the housing and movable between a locked position in which the lock piece is engaged with a stop surface protruding from the brake member, and an unlocked position in which the lock piece is disengaged from the stop surface.

9. The prosthetic knee of claim 8, further comprising a torsion spring biasing the lock piece toward the locked position.

10. The prosthetic knee of claim 8, further comprising a set screw extending at least in part through the housing, the set screw arranged to selectively prevent the lock piece from moving into the locking position.

11. The prosthetic knee of claim 10, wherein the set screw selectively engages the lock piece by a recess defined in an outer surface of the lock piece.

12. The prosthetic knee of claim 8, further comprising a cable threaded through the lock piece and arranged for manually moving the lock piece to the unlocked position.

13. The prosthetic knee of claim 1, wherein an inner surface of the housing defines at least one keyway comprising a slot or groove having a rectangular cross-section arranged to receive at least one corresponding key defined on the knee shaft.

14. The prosthetic knee of claim 1, further comprising a brake-play adjustment fastener situated on the chassis and engaging the brake member, the brake-play adjustment fastener arranged to selectively rotate the brake member about the second location point.

15. A prosthetic knee including:
a housing;

a chassis;
a brake member connected to the housing at a first location point and to the chassis at a second location point, the brake member arranged to prevent rotation of the housing relative to the chassis when the knee is loaded by a user in stance and defining a first pair of slots along a posterior surface of the brake member and a protruding step between the first slots;
a knee shaft extending through the brake member and secured to the housing, the knee shaft defining a second pair of slots along a posterior surface of the knee shaft corresponding in location to the location of the first slots;
a lock piece pivotally connected to the housing and movable between a locked position in which the lock piece is engaged with the stop surface to prevent rotation of the brake member relative to the housing, and an unlocked position in which the lock piece is disengaged from the stop surface; and
an extension assist system including a biasing mechanism located inside of the chassis and an extension assist link having a body portion operatively connected to the biasing mechanism and arm portions situated in the first slots defined by the brake member and the second slots defined by the knee shaft.

16. The prosthetic system of claim 15, wherein the biasing mechanism comprises an extension assist spring arranged to compress and push the knee back toward extension when the knee is in flexion.

17. The prosthetic knee of claim 16, further comprising a brake sleeve interposed between the brake member and the knee shaft.

18. The prosthetic knee of claim 16, further comprising:
a pylon attached to the chassis; and
an opening defined in a rear of the chassis, the opening arranged to provide access for adjusting compression of the biasing mechanism without removal of a pylon from the prosthetic knee.

19. A prosthetic system comprising:
a prosthetic socket arranged to receive a residual limb;
an adaptor connected to the prosthetic socket; and
a prosthetic knee connected to the adaptor, the prosthetic knee including:
a housing;
a chassis defining an opening in a rear thereof;
a brake member connected to the housing at a first location point and to the chassis at a second location point, the brake member defining a first pair of slots;
a knee shaft extending through the brake member and secured within a cavity defined by the housing, the knee shaft defining a second pair of slots along a posterior surface of the knee shaft corresponding in location to the first slots;
an extension assist system including:
a biasing mechanism located inside of the chassis; and
an extension assist link including a body portion operatively connected to the biasing mechanism and a pair of arm portions situated in the first slots defined by the brake member and in the second slots defined by the knee shaft, the arm portions are pivotally connected to the knee shaft at a third location point located within the second slots and a distance from the first location point; and
a pylon connected to the chassis, the opening in the chassis arranged to provide access for adjusting compression of the biasing mechanism without removal of the pylon from the chassis.

* * * * *